United States Patent [19]

Oharu et al.

[11] Patent Number: 5,710,317
[45] Date of Patent: Jan. 20, 1998

[54] PREPARATION OF DIFLUOROACETIC ACID FLUORIDE AND DIFLUOROACETIC ACID ESTERS

[75] Inventors: Kazuya Oharu; Seisaku Kumai, both of Yokohama, Japan

[73] Assignee: Asahi Glass Company Ltd., Tokyo, Japan

[21] Appl. No.: 506,730

[22] Filed: Jul. 26, 1995

[30] Foreign Application Priority Data

Jul. 28, 1994 [JP] Japan ............................ 6-177220
Jun. 29, 1995 [JP] Japan ............................ 7-164187

[51] Int. Cl.$^6$ ........................... C07C 69/63; C07C 53/21
[52] U.S. Cl. ........................... 560/227; 562/605; 568/683
[58] Field of Search ........................... 562/605; 560/227; 568/683

[56] References Cited

U.S. PATENT DOCUMENTS 2,409,315 10/1946 Rigby et al. ........................... 260/561
3,769,434 10/1973 Terrell ........................... 424/342

OTHER PUBLICATIONS

Park et al., "The Actions..Tetrafluoroethylene", J. Amer. Chem. Soc., vol. 73, No. 3, p. 1329, Mar. 1951.

Primary Examiner—Gary Geist
Assistant Examiner—Rosalynd A. Keys
Attorney, Agent, or Firm—Oblon, Spivak, McClelland, Maier & Neustadt, P.C.

[57] ABSTRACT

A method for preparing difluoroacetic acid fluoride, which comprises reacting a 1-alkoxy-1,1,2,2-tetrafluoroethane of the formula $HCF_2CF_2OR^1$ wherein $R^1$ is a $C_{1-4}$ alkyl group in a gas phase in the presence of a metal oxide catalyst.

18 Claims, No Drawings

PREPARATION OF DIFLUOROACETIC ACID FLUORIDE AND DIFLUOROACETIC ACID ESTERS

Difluoroacetic acid fluoride and difluoroacetic acid esters are compounds useful as various catalysts, as intermediates for drugs and agricultural chemicals and as intermediates for functional materials. The present invention relates to methods for preparing difluoroacetic acid fluoride and difluoroacetic acid esters and a method for preparing a 1-alkoxy-1,1,2,2-tetrafluoroethane as the starting material.

As a method for preparing difluoroacetic acid fluoride, there has been known (1) a method wherein difluoroacetic acid is reacted with phosphorus pentachloride or thionyl chloride, followed by a reaction with a metal fluoride such as potassium fluoride, (2) a method wherein a 1-alkoxy-1,1,2,2-tetrafluoroethane is decomposed in the presence of sulfur trioxide and fluorosulfuric acid (J. Fluorine Chem., 3, 63(1973)), or (3) a method wherein a 1-alkoxy-1,1,2,2-tetrafluoroethane is reacted in the presence of a catalyst such as an antimony halide or titanium halide (U.S. Pat. No. 4,357,282).

As a method for preparing difluoroacetic acid esters, there has been known (4) a method wherein difluoroacetic acid and an alcohol are esterified in the presence of an acid catalyst, or (5) a method wherein a 1-alkoxy-1,1,2,2-tetrafluoroethane is reacted with sulfuric acid and silica (J. Am. Chem. Soc., 72, 1860(1950)).

The methods (1) and (4) have a problem that the starting material difluoroacetic acid is not readily available. As a method for preparing difluoroacetic acid, (7) a method wherein chlorotrifluoroethylene as a starting material is reacted with an alkylamine, followed by hydrolysis to obtain chlorofluoroacetic acid amide, which is further fluorinated to difluoroacetic acid amide, followed by hydrolysis (Collect. Czech. Chem. Comm., 42(8), 2537(1977), CS180697) or (8) a method wherein ammonia is added to tetrafluoroethylene to obtain 2,4,6-difluoromethyl-1,3,5-triazine, followed by hydrolysis (U.S. Pat. No. 2,442,995, J. Org. Chem., 14, 751(1949)) has been reported.

However, the method (7) has problems such that the fluorination reaction of chlorofluoroacetic acid amide requires a long time and a high temperature, the post treatment after the fluorination is cumbersome, and the yield is low. On the other hand, the method (8) has a problem that the addition reaction of ammonia to tetrafluoroethylene is a reaction under a pressure as high as 34 kgG/cm$^2$, and it is practically impossible to conduct such a method on an industrial scale.

Further, each of the methods (7) and (8) requires a step of hydrolysis. When a step of hydrolysis by means of sulfuric acid is employed, a large amount of the resulting sulfuric acid waste liquid will be problematic. On the other hand, when a step of hydrolysis by means of an aqueous solution of an alkali metal hydroxide is employed, a mixture comprising difluoroacetic acid and water containing an inorganic salt, will be obtained, and difluoroacetic acid is required to be distilled from the inorganic salt since it has a higher boiling point than water, whereby the recovery rate is low.

In the method (2), the alkylfluorosulfate as a by-product of the reaction is highly toxic, and its treatment will be problematic. The method (3) has problems that the conversion in the reaction is low, and the catalyst is difficult to handle. In the method (5), control of the reaction is difficult, and corrosion of the reactor is an additional problem. The method (6) has a drawback that tetrafluoroethylene is introduced all at once at the initial stage, and the pressure at the initial stage of the reaction will be as high as 20 kgG/cm$^2$, and thus the reaction is rather dangerous.

The present inventors have conducted extensive studies to overcome the drawbacks of the above-mentioned conventional methods and as a result, have found methods whereby a 1-alkoxy-1,1,2,2-tetrafluoroethane, difluoroacetic acid fluoride and a difluoroacetic acid ester can be produced in good yield and on an industrial scale.

Thus, the present invention provides a method for preparing difluoroacetic acid fluoride, which comprises reacting a 1-alkoxy-1,1,2,2-tetrafluoroethane of the formula HCF$_2$CF$_2$OR$^1$ wherein R$^1$ is a C$_{1-4}$ alkyl group in a gas phase in the presence of a metal oxide catalyst.

Further, the present invention provides a method for preparing a difluoroacetic acid ester of the formula HCF$_2$COOR$^2$ wherein R$^2$ is a C$_{1-4}$ alkyl group, which comprises reacting a 1-alkoxy-1,1,2,2-tetrafluoroethane of the formula HCF$_2$CF$_2$OR$^1$ wherein R$^1$ is a C$_{1-4}$ alkyl group in a gas phase in the presence of a metal oxide catalyst to form difluoroacetic acid fluoride, and reacting the difluoroacetic acid fluoride with an alcohol of the formula R$^2$OH wherein R$^2$ is as defined above.

Furthermore, the present invention provides a method for preparing a 1-alkoxy-1,1,2,2-tetrafluoroethane of the formula HCF$_2$CF$_2$OR$^1$ wherein R$^1$ is a C$_{1-4}$ alkyl group, which comprises reacting an alcohol compound of the formula R$^1$OH wherein R$^1$ is as defined above and tetrafluoroethylene in the presence of a base, wherein the reaction is carried out while introducing the tetrafluoroethylene to the reaction system under a pressure of at most 3 kgG/cm$^2$.

Now, the present invention will be described in detail with reference to the preferred embodiments.

The 1-alkoxy-1,1,2,2-tetrafluroethane of the formula HCF$_2$CF$_2$OR$^1$ wherein R$^1$ is a C$_{1-4}$ alkyl group, as the starting material of the present invention, is a known compound (J. Am. Chem. Soc., 73, 1329(1951)), and it can be prepared by a method which comprises reacting the corresponding alcohol compound (R$^1$OH) with tetrafluoroethylene in the presence of a base.

In the present invention, it is preferred to employ a method wherein the reaction is carried out while introducing tetrafluoroethylene under a pressure of at most 3 kgG/cm$^2$, particularly from 0 to 3 kgG/cm$^2$, to the reaction system. The method of introducing tetrafluoroethylene at such a low pressure is advantageous not only from the viewpoint that the reaction can be safely carried out, but also from the viewpoint that the yield tends to be higher than the conventional method.

As the base to be used in this reaction, an alkali metal hydroxide is preferred. Particularly preferred is sodium hydroxide or potassium hydroxide. The base may be used as diluted with water, or an inexpensive 85% product for industrial use may also be employed.

By this method, the 1-alkoxy-1,1,2,2-tetrafluoroethane is prepared in a higher yield than the one prepared by the conventional method and with a less amount of by-products, whereby the reaction product can be readily purified simply by washing with water. The following compounds may be mentioned as specific examples of the 1-alkoxy-1,1,2,2-tetrafluoroethane to be obtained. However, useful compounds are not limited to such specific examples.

1-Methoxy-1,1,2,2-tetrafluoroethane, 1-ethoxy-1,1,2,2-tetrafluoroethane, 1-(n-propoxy)-1,1,2,2-tetrafluoroethane, 1-isopropoxy-1,1,2,2-tetrafluoroethane, and 1-(n-butoxy)-1,1,2,2-tetrafluoroethane.

In the present invention, the above 1-alkoxy-1,1,2,2-tetrafluoroethane is subjected to a gas phase reaction in the presence of a metal oxide catalyst. This reaction may be represented by the following formula:

$$HCF_2CF_2OR^1 \rightarrow HCF_2COF + R^1F$$

The metal oxide catalyst is not particularly limited so long as it is a metal oxide which is capable of efficiently promoting the above reaction. As the metal component in the metal oxide, aluminum, zirconium or titanium is preferred. The metal oxide catalyst is preferably at least one metal oxide catalyst selected from the group consisting of alumina ($Al_2O_3$), zirconia ($ZrO_2$) and titania ($TiO_2$). Particularly preferred is alumina in view of the reactivity and the useful life of the catalyst.

The metal oxide catalyst of the present invention may contain other atoms than the metal component and oxygen. As such other atoms, a fluorine atom and a chlorine atom are, for example, preferred. For example, the metal oxide catalyst may be partially fluorinated alumina, partially chlorinated alumina, partially fluorinated and chlorinated alumina, partially fluorinated zirconia or partially fluorinated titania. The proportion of the chlorine atom or the fluorine atom in the metal oxide catalyst is not particularly limited.

The metal oxide catalyst is used usually in the form of particles. The particle size is not particularly limited and is usually at a level of from 20 µm to 5 mm. When the metal oxide catalyst contains chlorine atoms or fluorine atoms, such chlorine atoms or fluorine atoms may be present only on the surface of the metal oxide catalyst.

The metal oxide catalyst is preferably subjected to activation treatment prior to the reaction of the present invention. The activation treatment may be a common method and is not particularly limited. As such activation treatment, it is preferred to sufficiently dehydrate the catalyst in a nitrogen stream at a temperature of from 250° C. to 300° C. and to activate it with dichlorodifluoromethane (hereinafter referred to as R12), chlorodifluoromethane or hydrogen fluoride. It is believed that by such activation treatment, a metal oxide catalyst is formed which contains atoms other than the metal component and oxygen on the surface or in the entirety of the metal oxide catalyst.

The reaction of $HCF_2CF_2OR^1$ with the metal oxide catalyst is carried out in a gas phase. Further, in that reaction, an inert gas may be present. As such an inert gas, nitrogen or a rare gas may, for example, be mentioned. In view of the handling efficiency and availability, nitrogen or helium is preferred. When such an inert gas is used, the amount thereof is not particularly limited. However, if it is too much, the recovery rate may decrease. Therefore, in a usual case, it is preferred that the inert gas is present in an amount of at most 50 vol % in the total amount including the vaporized product of the starting material 1-alkoxy-1,1,2,2-tetrafluoroethane.

The reactor to be used for carrying out the reaction of $HCF_2CF_2OR^1$ with the metal oxide catalyst is preferably of a fixed bed type or a fluidized bed type, and the reactor may suitably be changed depending upon the type or the amount of the reactant.

The reaction temperature of $HCF_2CF_2OR^1$ with the metal oxide catalyst varies depending upon the type of the catalyst and the starting material. However, it is usually at a level of from 100° to 300° C., preferably from 150° to 250° C. This reaction is an endothermic reaction, whereby the conversion tends to be low when the reaction temperature is low. The reaction time is usually from 0.1 to 300 seconds, preferably from 2 to 60 seconds. If the reaction time is too short, the conversion tends to be low. On the other hand, if it is too long, formation of by-products tends to increase. The reaction pressure is not particularly limited and may be atmospheric pressure, reduced pressure or elevated pressure. In a usual case, the pressure is at a level of from 0.5 to 5 atm.

In the reaction of $HCF_2CF_2OR^1$ with the metal oxide catalyst of the present invention, in addition to the desired difluoroacetic acid fluoride, an alkylfluoride as well as its decomposition products such as an olefin and hydrogen fluoride, will usually form as by-products. Further, in some cases, a difluoroacetic acid alkyl ester or difluoroacetic acid will form. Accordingly, the crude product obtained by the reaction is usually preferably subjected to purification treatment.

The method for purification treatment of difluoroacetic acid fluoride is not particularly limited. Difluoroacetic acid fluoride can readily be purified, for example, by contacting the crude reaction product with a tertiary amine or sodium fluoride pellets to remove hydrogen fluoride, followed by distillation. When difluoroacetic acid fluoride is used as the starting material for the next step, such purification treatment may sometimes be omitted.

The reaction of $HCF_2CF_2OR^1$ with the metal oxide catalyst of the present invention provides a very high conversion and is excellent also in the reproducibility of the result of the reaction. Further, it is a reaction of a gas phase continuous flow system and thus is efficient and excellent also from the viewpoint of the productivity.

Difluoroacetic acid fluoride can be led to other useful compound by reacting it with other compound reactive with its terminal —COF group. For example, difluoroacetic acid fluoride can be converted to a difluoroacetic acid ester of the formula $HCF_2COOR^2$ wherein $R^2$ is a $C_{1-4}$ alkyl group, by reacting it with an alcohol of the formula $R^2OH$. This reaction may be represented by the following formula:

$$HCF_2COF + R^2OH \rightarrow HCF_2COOR^2 + HF$$

Specific examples of the alcohol of the formula $R^2OH$ include methanol, ethanol, 1-propanol, 2-propanol, 1-butanol and 2-butanol. However, it is not limited to such specific examples.

The reaction of $HCF_2COF$ with $R^2OH$ can be carried out either by a gas phase reaction or by a liquid phase reaction. Usually, it is preferably carried out by a liquid phase reaction. As a reactor for the liquid phase reaction, a batch-system reactor or an absorption tower-system reactor is preferred. The reaction temperature is preferably from 0° to 50° C., and the reaction pressure is preferably from −1 to 3 kgG/cm². Usually, the reaction is preferably conducted under atmospheric pressure.

The reaction of $HCF_2COF$ with $R^2OH$ can be carried out in the presence or absence of a solvent for the reaction. It is preferably carried out in the absence of a solvent. When the reaction is carried out in the presence of a solvent, such a solvent is preferably an aprotic solvent.

Further, a tertiary amine or the like may be present in the reaction system in order to remove hydrogen fluoride as a by-product or hydrogen fluoride brought in from the reaction of the previous stage of $HCF_2CF_2OR^1$ with the metal oxide catalyst. As such a tertiary amine, an amine of the formula $R^3R^4R^5N$ wherein each of $R^3$, $R^4$ and $R^5$ which may be the same or different, is an alkyl group or an aryl group, is preferred. Particularly preferred is a trialkylamine or a (dialkyl)(phenyl)amine. Particularly, triethylamine, tripropylamine or N,N-dimethylaniline may, for example, be mentioned. The amount of the tertiary amine is preferably at most 2 mols per mol of $HCF_2CF_2OR^1$. By the presence of such a tertiary amine, the conversion of the reaction can substantially be increased.

The difluoroacetic acid ester ($HCF_2COOR^2$) formed by the reaction of $HCF_2COF$ with $R^2OH$ has an azeotropic nature of boiling together with the corresponding alcohol ($R^2OH$) used for the reaction. Accordingly, when it is desired to obtain a difluoroacetic acid ester containing substantially no alcohol, (a) difluoroacetic acid fluoride is contacted to the difluoroacetic acid ester containing $R^2OH$ to let it react with $R^2OH$, to obtain a difluoroacetic acid ester of high purity containing substantially no $R^2OH$, or (b) $R^2OH$ or the like may be removed by a combination of washing with water and distillation. Among these methods, the method (a) is preferred, since it is free from a problem such as treatment of a waste liquid resulting from the purification treatment.

The method (a) is preferably carried out by a reactor of absorption tower system. Particularly, it is preferably conducted by the following method when the reaction is to be carried out continuously on an industrial scale.

Firstly, an absorption tower A and an absorption tower B are arranged in series. To the absorption tower A, $R^2OH$ or a difluoroacetic acid ester containing $R^2OH$ is charged, and to the absorption tower B, $R^2OH$ is charged. As a first step, difluoroacetic acid fluoride is introduced to the absorption tower A, whereby difluoroacetic acid fluoride and $R^2OH$ are reacted to form a difluoroacetic acid ester. Consequently, in the absorption tower A, $R^2OH$ decreases. Then, unreacted difluoroacetic acid fluoride is supplied to the absorption tower B. To the absorption tower B having $R^2OH$ charged therein, the difluoroacetic acid fluoride discharged from the absorption tower A is introduced, whereby $R^2OH$ and difluoroacetic acid fluoride are reacted to form a difluoroacetic acid ester containing $R^2OH$. When a difluoroacetic acid ester containing substantially no $R^2OH$ is formed in the absorption tower A, the difluoroacetic acid ester is withdrawn.

In a second step, the absorption tower B having the difluoroacetic acid ester containing $R^2OH$ obtained in the first step charged therein, is used as an absorption tower A in the second step. To the absorption tower A in the first step, $R^2OH$ is charged to obtain an absorption tower B in the second step. The same operation as in the first step is then carried out. Further, the same operation as in the first and second steps, is sequentially repeated to continuously produce a difluoroacetic acid ester of high purity.

The above method is advantageous in that a continuous operation is thereby possible. Further, it is particularly preferred, since it is free from a problem of e.g. waste liquid treatment. The obtained difluoroacetic acid ester is usually preferably subjected to removal of hydrogen fluoride and by-products by distillation to obtain a final product.

In a case where the reaction of $R^2OH$ with the difluoroacetic acid ester is carried out by a batch system reactor, it is preferred to conduct purification treatment by the method (b). Namely, it is preferred that the crude reaction solution containing the difluoroacetic acid ester is firstly washed with water to remove $R^2OH$ and then subjected to distillation.

The method for preparing a difluoroacetic acid ester of the present invention is an excellent method whereby a difluoroacetic acid ester of high purity can be obtained at a high conversion. Further, in a case where $R^1$ of $CF_2CF_2OR^1$ and $R^2$ of $R^2OH$ are the same alkyl groups, the difluoroacetic acid alkyl ester ($HCF_2COOR^1$) which usually forms as a by-product in the reaction of $HCF_2CF_2OR^1$ with the metal oxide catalyst and the difluoroacetic acid ester ($HCF_2COOR^2$) as the desired product of the subsequent reaction will be the same. Accordingly, it is unnecessary to conduct purification treatment after the reaction of $HCF_2CF_2OR^1$ with the metal oxide catalyst. Thus, the method is efficient and has an additional merit that the overall yield increases to some extent.

In the present invention, each reaction step is excellent in the reproducibility of the result of the reaction. Further, the reactions of the present invention can be combined in such a manner that difluoroacetic acid fluoride is continuously produced and supplied to the next reaction, and therefore, they can be employed for an industrial continuous production method. Further, the reaction for preparing a difluoroacetic acid ester containing substantially no $R^2OH$, is particularly excellent for an industrial production method in which the reaction can be conducted all at once with a large capacity.

The difluoroacetic acid fluoride and the difluoroacetic acid ester obtained by the present invention are very useful compounds which can be used for e.g. various catalysts, intermediates for drug and agricultural chemicals and intermediates for functional materials.

For example, the difluoroacetic acid fluoride can be converted to various useful compounds by a reaction with other compounds having groups reactive with —COF group. As such other compounds, compounds having hydroxyl groups, primary amino groups, secondary amino groups, imine groups or groups of =NOH, or salts of such compounds, are preferred.

For example, difluoroacetic acid fluoride may be reacted with a compound having a corresponding imino group to prepare an iminothiazoline compound of the following formula. This compound is a useful compound disclosed as a herbicide in U.S. Pat. No. 5,244,863.

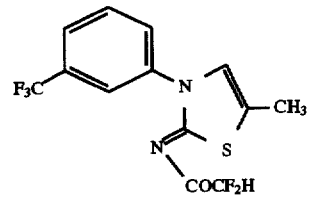

When difluoroacetic acid fluoride is reacted with other compounds, hydrogen fluoride will form. Therefore, it is preferred to conduct the reaction in the presence of the above-mentioned tertiary amine or the like.

Now, the present invention will be described in further detail with reference to Examples. However, it should be understood that the present invention is by no means restricted by such specific Examples. Example 22 is a Reference Example.

EXAMPLE 1

Preparation of 1-methoxy-1,1,2,2-tetrafluoroethane

Into a 10 l autoclave made of Hastelloy C, 659 g (10 mols) of 85% potassium hydroxide and 2,260 g (70.6 mols) of methanol were charged, and the interior was thoroughly flushed with nitrogen. Then, tetrafluoroethylene was fed, while controlling the reaction temperature at a level of not higher than 40° C. and the reactor pressure at a level of from 2 to 3 kgG/cm² so that it did not exceed 3 kgG/cm². The reaction proceeded exothermically. Nine hours later, the reaction was terminated when the amount of tetrafluoroethylene fed, reached 6,139 g (61.4 mols). The crude reaction solution was washed 3 times with 2 kg of water to obtain 7,296 g (55.3 mols, yield: 90%) of 1-methoxy-1,1,2,2-tetrafluoroethane having a purity of 99.7%.

EXAMPLE 2

Preparation of 1-methoxy-1,1,2,2-tetrafluoroethane

The reaction was carried out in the same manner as in Example 1 except that the amount of methanol was changed to 2,990. Eight hours later, the reaction was terminated when the amount of tetrafluoroethylene fed, reached 5,465 g (54.6 mols). The crude reaction solution was washed 3 times with 2 kg of water to obtain 7,378 (50.5 mols, yield: 92.5%) of 1-methoxy-1,1,2,2-tetrafluoroethane having a purity of 99.7%.

EXAMPLE 3

Preparation of 1-ethoxy-1,1,2,2-tetrafluoroethane

The reaction was carried out in the same manner as in Example 1 except that 4,300 g of ethanol was used instead of 2,260 g of methanol. Eight hours later, the reaction was terminated when the amount of tetrafluoroethylene fed, reached 5,465 g (54.6 mols). The crude reaction solution was washed 3 times with 2 kg of water to obtain 1-ethoxy-1,1,2,2-tetrafluoroethane having a purity of 99.7% in a yield of 94.5%.

EXAMPLES 4 to 8

Preparation of difluoroacetic acid fluoride

A U-shaped reaction tube made of Inconel 600 and having an inner diameter of 2.54 cm and a length of 100 cm, which was packed with 300 cc of γ-alumina, was immersed in a salt bath and activated at 250° C. in a nitrogen stream for 12 hours and in a $R^{12}$ stream for 12 hours. 1-Ethoxy-1,1,2,2-tetrafluoroethane was vaporized by a preheater and introduced under atmospheric pressure into the reactor. The reaction temperature (the salt bath temperature) and the residence time in the reaction tube are shown in Table 1. Upon expiration of 30 minutes after the initiation of the reaction, the crude reaction gas was analyzed by a NMR method, whereby formation of difluoroacetic acid fluoride was confirmed. The analytical results by a gas chromatograph method (FID detector, the same applies in the following Examples) are shown in Table 1.

TABLE 1

| Example No. | 4 | 5 | 6 | 7 | 8 |
|---|---|---|---|---|---|
| Reaction temperature (°C.) | 200 | 200 | 200 | 150 | 250 |
| Residence time (sec) | 15 | 8 | 4 | 15 | 15 |
| Conversion (%) | 100 | 99.8 | 77.5 | 85.2 | 100 |
| Selectivity (%) | 99.4 | 99.6 | 99.7 | 99.7 | 98.5 |

EXAMPLES 9 to 11

Preparation of difluoroacetic acid fluoride

The reaction was carried out in the same manner as in Example 4 except that instead of 1-ethoxy-1,1,2,2-tetrafluoroethane in Example 4, 1-methoxy-1,1,2,2-tetrafluoroethane was used, and the reaction was conducted at the reaction temperature for the residence time as identified in Table 2, whereupon formation of difluoroacetic acid fluoride was confirmed. The analytical results of the reaction product are shown in Table 2.

EXAMPLE 12

Preparation of difluoroacetic acid fluoride

The reaction was carried out in the same manner as in Example 4 except that instead of 1-ethoxy-1,1,2,2-tetrafluoroethane, 1-isopropoxy-1,1,2,2-etrafluoroethane was used, whereupon formation of difluoroacetic acid fluoride was confirmed. The analytical results of the reaction product are shown in Table 2.

EXAMPLE 13

Preparation of difluoroacetic acid fluoride

The reaction was continued under the same conditions as in Example 4, and upon expiration of 280 hours, the crude reaction gas was analyzed, whereby formation of difluoroacetic acid fluoride was confirmed. The analytical results of the reaction product are shown in Table 2.

TABLE 2

| Example No. | 9 | 10 | 11 | 12 | 13 |
|---|---|---|---|---|---|
| Reaction temperature (°C.) | 200 | 200 | 250 | 200 | 200 |
| Residence time (sec) | 15 | 30 | 15 | 15 | 15 |
| Conversion (%) | 97.5 | 99.8 | 100 | 100 | 99.5 |
| Selectivity (%) | 98.9 | 98.7 | 97.5 | 95.9 | 99.6 |

EXAMPLE 14

Preparation of difluoroacetic acid fluoride

The reaction was carried out in the same manner as in Example 4 except that instead of 300 cc of γ-alumina, 300 cc of zirconia was used, whereupon formation of difluoroacetic acid fluoride was confirmed. The analytical results of the reaction product are shown in Table 3.

EXAMPLES 15 to 17

Preparation of difluoroacetic acid fluoride

The reaction was carried out in the same manner as in Example 14 except that the residence time was changed to 8 seconds (Example 15), the crude reaction gas upon expiration of 50 hours after the initiation of the reaction, was analyzed (Example 16) or the reaction temperature was changed to 220° C. (Example 17), whereupon formation of difluoroacetic acid fluoride was confirmed. The analytical results of the reaction product are shown in Table 3.

EXAMPLE 18

Preparation of difluoroacetic acid fluoride

The reaction was carried out in the same manner as in Example 14 except that instead of 1-ethoxy-1,1,2,2-tetrafluoroethane, 1-methoxy-1,1,2,2-tetrafluoroethane was used, and the reaction temperature was changed to 250° C., whereupon formation of difluoroacetic acid fluoride was confirmed. The analytical results of the reaction product are shown in Table 3.

TABLE 3

| Example No. | 14 | 15 | 16 | 17 | 18 |
|---|---|---|---|---|---|
| Reaction temperature (°C.) | 200 | 200 | 200 | 220 | 250 |
| Residence time (sec) | 15 | 8 | 15 | 15 | 15 |
| Conversion (%) | 100 | 89.9 | 84.3 | 98.7 | 56.1 |
| Selectivity (%) | 99.7 | 99.6 | 99.7 | 99.5 | 97.8 |

EXAMPLE 19

Preparation of ethyl difluoroacetate

The crude reaction gas (the main component was difluoroacetic acid fluoride) of Example 4 was bubbled at 10° C.

in a 2 l plastic bottle charged with 146 g (3.0 mols) of ethanol and 303 g (3.0 mols) of triethylamine. Then, 365 g (2.5 mols) of 1-ethoxy-1,1,2,2-tetrafluoroethane was fed over a period of about 75 minutes. Then, nitrogen was supplied to the gas phase reactor at a rate of 200 cc/min for 20 minutes. The crude reaction solution of the plastic bottle was washed with 2 l of water, and the organic layer and the aqueous layer were separated. The aqueous layer was extracted with 300 cc of methylene chloride, and the methylene chloride layer and the organic layer were put together and subjected to distillation to obtain 285 g (yield: 91.9%) of ethyl difluoroacetate (boiling point: 101° C.) having a purity of at least 99.5%.

EXAMPLE 20

Preparation of ethyl difluoroacetate

The reaction was carried out in the same manner as in Example 19 except that instead of the crude reaction gas of Example 4, the crude reaction gas of Example 14 was used, whereby 280 g (yield: 90.3%) of ethyl difluoroacetate having a purity of at least 99.5% was obtained.

EXAMPLE 21

Preparation of ethyl difluoroacetate

A U-shaped reaction tube made of Inconel 600 and having an inner diameter of 2.54 cm and a length of 100 cm, which was packed with 300 cc of γ-alumina, was immersed in a salt bath of 200° C., and about 4.5 g per minute of 1-ethoxy-1,1,2,2-tetrfluoroethane was vaporized by a preheater and introduced into the reaction tube under atmospheric pressure.

Two absorption towers (A and B) made of Teflon were arranged in series so that the crude reaction gas containing difluoroacetic acid fluoride withdrawn from the reaction tube would pass therethrough, and the crude reaction gas was introduced from the absorption tower A. Into each of the towers A and B, 920 g of ethanol was introduced. As a first step, the liquid and the gas were circulated at 50° C. so that the contact time of the liquid and the gas became about 5 seconds. Eighteen hours later, the amount of ethanol in the absorption tower A was at most 100 ppm, and the amount of ethanol in the absorption tower B was analyzed by gas chromatography and found to be 20.3 area %. The reaction solution in the absorption tower A was distilled by a stainless steel distillation column to obtain 2,580 g of ethyl difluoroacetate.

As a second step, the absorption tower B of the first step was used as an absorption tower A, and 920 g of ethanol was introduced to the absorption tower A of the first step from which ethyl difluoroacetate was withdrawn, whereupon this tower was used as an absorption tower B. The crude reaction gas was circulated in the same manner as in the first step. When the amount of ethanol in the absorption tower A became not more than 100 ppm, the reaction was terminated. At that time, the amount of ethanol in the absorption tower B was 20.4 area %. The reaction solution in the absorption tower A was distilled by a stainless steel distillation column to obtain 2,600 g of ethyl difluoroacetate.

EXAMPLE 22

Preparation of N,N-diethyl difluoroacetic acid amide

A U-shaped reaction tube made of Inconel 600 and having an inner diameter of 2.54 cm and a length of 100 cm, which was packed with 300 cc of γ-alumina, was immersed in a salt bath and activated at 250° C. in a nitrogen stream for 12 hours and then in a $R^{12}$ stream for 12 hours. 1-Ethoxy-1,1,2,2-tetrafluoroethane prepared in Example 3 was vaporized by a preheater and introduced into the reaction tube under atmospheric pressure. The reaction temperature (the salt bath temperature) was 200° C., and the residence time in the reaction tube was 15 seconds.

The crude reaction gas was bubbled at 10° C. in a 2 l plastic bottle charged with 219 g (3.0 mols) of diethylamine, 303 g (3.0 mols) of triethylamine and 300 g of methylene chloride. Then, 365 g (2.5 mols) of 1-ethoxy-1,1,2,2-tetrafluoroethane was fed over a period of about 75 minutes. Then, nitrogen was supplied to the gas phase reactor at a rate of 200 cc/min for 20 minutes. The crude reaction solution was washed with 2 l of water, and the aqueous phase was extracted with 300 g of methylene chloride. The organic layers were put together and distilled to obtain 353 g (yield: 93.5%) of N,N-diethyl difluoroacetic acid amide (boiling point: 64° C./11 torr) having a purity of at least 99.5%.

The reactions of the present invention all provide very high conversion and selectivity, and they are excellent reactions having good reproducibility of the results of the reactions. Further, the reactions can be carried out continuously and quantitatively and thus are suitable for an industrial production method. Furthermore, the reactions of the present invention can be carried out under safe conditions and thus provide a highly practical method.

What is claimed is:

1. A method for preparing difluoroacetic acid fluoride, which comprises reacting a 1-alkoxy-1,1,2,2-tetrafluoroethane of the formula $HCF_2CF_2OR^1$ wherein $R^1$ is a $C_{1-4}$ alkyl group in a gas phase in the presence of a metal oxide catalyst.

2. The method according to claim 1, wherein the metal oxide catalyst is at least one member selected from the group consisting of alumina, zirconia and titania.

3. The method according to claim 1, wherein the metal oxide catalyst is alumina.

4. The method according to claim 1, wherein $R^1$ is an ethyl group.

5. The method according to claim 2, wherein $R^1$ is an ethyl group.

6. The method according to claim 3, wherein $R'$ is an ethyl group.

7. A method for preparing a difluoroacetic acid ester of the formula $HCF_2COOR^2$ wherein $R^2$ is a $C_{1-4}$ alkyl group, which comprises reacting a 1-alkoxy-1,1,2,2-tetrafluoroethane of the formula $HCF_2CF_2OR^1$ wherein $R^1$ is a $C_{1-4}$ alkyl group in a gas phase in the presence of a metal oxide catalyst to form difluoroacetic acid fluoride, and reacting the difluoroacetic acid fluoride with an alcohol of the formula $R^2OH$ wherein $R^2$ is as defined above.

8. The method for preparing a difluoroacetic acid ester according to claim 7, wherein a tertiary amine is present together with the alcohol of the formula $R^2OH$.

9. The method for preparing a difluoroacetic acid ester according to claim 7, wherein $R^2$ is an ethyl group.

10. The method for preparing a difluoroacetic acid ester according to claim 8, wherein $R^2$ is an ethyl group.

11. The method for preparing a difluoroacetic acid ester according to claim 7, wherein $R^1$ and $R^2$ are the same alkyl groups.

12. The method for preparing a difluoroacetic acid ester according to claim 8, wherein $R^1$ and $R^2$ are the same alkyl groups.

13. The method for preparing a difluoroacetic acid ester according to claim 9, wherein $R^1$ and $R^2$ are the same alkyl groups.

14. The method for preparing a difluoroacetic acid ester according to claim 10, wherein $R^1$ and $R^2$ are the same alkyl groups.

15. A method for producing a difluoroacetic acid ester containing substantially no alcohol, which comprises reacting a mixture of a difluoroacetic acid ester of the formula $HCF_2COOR^2$ wherein $R^2$ is a $C_{1-4}$ alkyl group containing an alcohol of the formula $R^2OH$ wherein $R^2$ is as defined above with difluoroacetic acid fluoride.

16. The method according to claim 15, wherein said reaction is carried out in the liquid phase at a temperature of from 0° to 50° C.

17. The method of claim 15, wherein said reaction is carded out in the presence of an aprotic solvent.

18. The method of claim 15, wherein said reaction is carried out in the presence of a tertiary amine.

* * * * *